US008892363B2

(12) United States Patent
Keller et al.

(10) Patent No.: US 8,892,363 B2
(45) Date of Patent: Nov. 18, 2014

(54) METHOD OF USING DENSITY MAPS BASED ON MARKER VALUES FOR THE DIAGNOSIS OF PATIENTS WITH DISEASES, AND IN PARTICULAR TUMORS

(75) Inventors: Thomas Keller, Leipzig (DE); Hermann Butz, Lich (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1753 days.

(21) Appl. No.: 11/569,950

(22) PCT Filed: Jun. 1, 2005

(86) PCT No.: PCT/EP2005/005877
§ 371 (c)(1),
(2), (4) Date: Oct. 16, 2007

(87) PCT Pub. No.: WO2005/119564
PCT Pub. Date: Dec. 15, 2005

(65) Prior Publication Data
US 2008/0113332 A1    May 15, 2008

(30) Foreign Application Priority Data

Jun. 4, 2004    (DE) .................. 10 2004 027 429

(51) Int. Cl.
*G01N 33/48* (2006.01)
*C12Q 1/00* (2006.01)

(52) U.S. Cl.
USPC ............................... 702/19; 435/4

(58) Field of Classification Search
None
See application file for complete search history.

(56) References Cited

U.S. PATENT DOCUMENTS

| 5,501,983 A | 3/1996 | Lilja et al. |
| 2003/0233197 A1 | 12/2003 | Padilla et al. |

FOREIGN PATENT DOCUMENTS

WO    WO 02/095650    11/2002

OTHER PUBLICATIONS

Fraley et al. (Technical report No. 380, Department of Statistics, University of Washington, Oct. 2000).*
Allard et al. (Clinical Chemistry, vol. 44, No. 6, p. 1216-1223, 1998).*
Dhanasekaran et al. (Nature, vol. 412, p. 822-826, Aug. 23, 2001).*
Partin et al. (Urology vol. 48, No. 6a, p. 55-61, 1996).*
Jung et al. "Ratio of Free or Complexed Prostate-specific Antigen (PSA) to Total PSA: Which Ratio Improves Differentiation between Benign Prostatic Hyperplasia and Prostate Cancer?" (Clinical Chemistry, vol. 46 (2000) pp. 55-62).*
Kelsall et al. "Kernel estimation of relative risk" (Bernoulli, vol. 1 (1995) pp. 003-006).*
Scott, David W., Chapter 9 Other Applications, Multivariate Density Estimation, 1992, pp. 247-265, John Wiley & Sons, Inc.
Hastie, Discriminant Analysis by Gaussian Mixtures, Journal of the Royal Statistical Society, vol. 58, No. 1, 1996, pp. 155-176, Blackwell Publishing.
Mangasarian, Olvi L., Breast Cancer Diagnosis and Prognosis Via Linear Programming, Operations Research, vol. 43, No. 4, Jul.-Aug. 1995, pp. 570-579.
McLachlan, Geoffry J., Discriminant Analysis and Statistical Pattern Recognition, 2004, pp. 1-545, John Wiley & Sons, Inc.
English Version of PCT Preliminary Report on Patentability, Dec. 28, 2006, 5 pgs.

* cited by examiner

*Primary Examiner* — Anna Skibinsky
(74) *Attorney, Agent, or Firm* — Kevin Stein

(57) ABSTRACT

The invention relates to a method of using density maps based on marker values, and in particular tumor markers and other indicator substances/values for the diagnosis of patients with diseases, in particular tumorous diseases, and especially prostate carcinoma.

9 Claims, 7 Drawing Sheets

Figure 1:
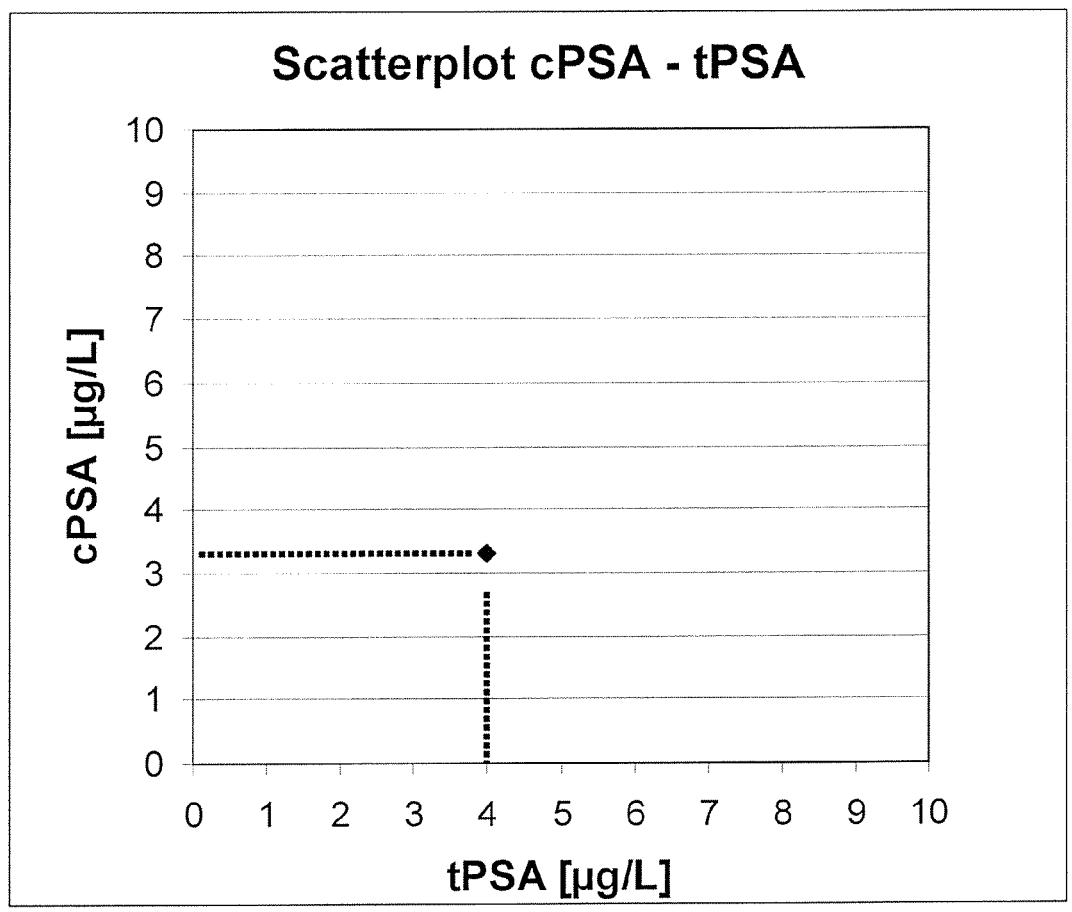

METHOD OF USING DENSITY MAPS BASED ON MARKER VALUES FOR THE DIAGNOSIS OF PATIENTS WITH DISEASES, AND IN PARTICULAR TUMORS

The invention relates to a method of using density maps based on tumour marker values and other indicator substances/values for the diagnosis of patients with tumourous diseases, and in particular prostate carcinoma. The invention relates in particular to the use of a mathematical procedure with the aid which the risk of a patient suffering from a tumour can be assessed on the basis of pairs of tumour marker values.

The invention is based on the problem of assessing the risk, expressed as a positive prognostic value, for a specific clinical use situation, of a patient suffering from a tumour and in particular from prostate carcinoma by means of a density map based an tumour marker values or other indicator substances/values determined for the patient.

According to the prior art, the diagnosis of tumours, and in particular prostate carcinoma, on the basis of tumour markers and other indicator substances/values, has so far been performed in the following manner:
a) an indicator substance is analyzed, the level of which correlates with the existence of a tumourous disease. With the aid of a cut-off value determined from a study population, the patient is assigned to the malignant or benign group, depending on the position of the measured value above or below the cut-off value;
b) several indicator substances or tumour marker values are analyzed and a decision tree is used for making several decisions according to a), or they are combined by means of mathematical procedures (e.g. fuzzification/EP 0922266 B1) and then assigned with regard to malignancy and histology, with the aid of an artificial cut-off value (e.g. between 0 and 1);
c) two indicator substances or tumour marker values are determined and a ratio calculated therefrom. This ratio correlates to a greater degree than a single tumour marker with the existence of a tumourous disease. With the aid of a cut-off value for this ratio, determined from a study population, a decision according to a) is made;
d) in addition to the indicator substances or tumour markers, parameters are included (such as for example age) which affect either the clinical picture or the analytical properties of the indicator substances;
e) complex computational methods (e.g. neural networks), into which tumour marker values and indicator substances/values are entered, are used in order to improve the sensitivity and/or specificity of the diagnostic results.

Most of the prior art inventions relating to prostate carcinomas describe the analysis of tumour marker values as well as the use of these values and their ratios for diagnostic purposes:

One example which may be mentioned is U.S. Pat. No. 5,501,983, which relates to ratios of free PSA (fPSA) and complexed PSA (cPSA).

The solutions provided according to the prior art are distinguished by the general existence of a large overlapping area between patients with and without tumours, between the abovementioned tumour markers and indicator substances/values and between the mathematical values. The more effective the subdivision of the overlapping area, the more effective the solution provided.

All of the methods so far disclosed, which use several tumour markers, do not subdivide the overlapping area in an optimum manner. In addition, the overlapping area is usually presented either inadequately (e.g. in the form of scatterplots) or not at all. Where modelling, such as mathematical modelling, is employed, this can only be used in the field of clinical diagnostics to provide a probability reading which cannot be directly applied to the patent's situation.

The use of complex methods (e.g. neural networks) produces better results but is too dependent on individual data.

Thus, all of the solutions based on more than one marker or indicator substance/value have the disadvantage of not adequately defining the risk of having a tumour. The results provided by the proposed solutions are either in the form of a measured value or a deduced value which, while correlating with the risk of having a tumour, do not define the risk directly in the form of a positive prognostic value.

The above problem is solved according to the invention in that for the subsequent process steps indicator substances are used which, depending on their nature, are either produced by tumour cells or induced in other body cells by the tumour, or the concentrations of these non-tumour-specific substances are changed by the tumour concerned, wherein the measured values for said indicator substances are determined by direct substance analysis, and in that
(2) the measured values for the indicator substances are, depending on their number, plotted in a two- or higher-dimensional scatterplot and,
(3) with the aid of stored, diagnostically confirmed data blocks which are processed mathematically with the aid of the kernel-density method and form a density map in the said scatterplot, are they assigned to a density which
(4) corresponds to a risk, defined by the positive prognostic value, of suffering from a tumour in a specific clinical use situation (such as a screening situation, the initial clinical diagnosis or a check-up).

It is advantageous for the indicator substances for the diagnosis of prostate carcinoma to be tumour markers which are free or bound forms or molecular moieties of the prostate-specific antigen (PSA). Thus, the two-dimensional density maps for the following pairs, cPSA-tPSA, fPSA-tPSA or cPSA-fPSA, may be explicitly mentioned for the diagnosis of prostate carcinoma. In addition, it is also possible to use mathematical values obtained from indicator substances as indicator values. Thus the values fPSA/tPSA (quotient), cPSA/tPSA (quotient) or tPSA–fPSA (difference) can be used as indicator values which are plotted against one—in this case together with one of the abovementioned parameters—or both axes of a 2D density map.

The invention is explained in more detail by means of three practical examples. For each example, macromolecules from blood or other body fluids are used as indicator substances which, depending on their nature, are either produced from tumour cells or formed in other body cells by the tumour, or the concentrations of these non-tumour-specific substances are changed by the tumour. The measured values of the indicator substances are determined by direct substance analysis. In addition, indicator values are included which correlate with the clinical picture (e.g. anatomical changes) or affect the analytical properties of the tumour marker or indicator substances (e.g. age). In the practical examples the further process steps for determining the positive prognosis are determined.

The invention can also be used for the diagnosis and differential diagnosis of other tumours. For example, in the diagnosis of bronchial carcinoma the tumour marker pairs CYFRA 21-1 and ProGRP, CYFRA 21-1 and NSE or tripel, are used, CEA being additionally determined. For the differential diagnosis of small cell or non-small cell bronchial carcinoma a density map can be used which is also based on the tumour marker pairs CYFRA 21-1 and ProGRP or CYFRA 21-1 and NSE. For differential diagnosis within non-small cell tumours (such as adenocarcinoma or squamous epithelial carcinoma) a density map can be used which is based on the marker pairs CYFRA 21-1 and CEA or SCC and CEA.

In addition, the use of the invention is not restricted to tumours. Density maps can for example be used for the diagnosis or prognostic assessment of severe inflammatory processes, for which, for example, inflammation laboratory parameters such as CRP, IL-6 (or other cytokine markers) are used. An additional indicator value which can be used is a score value (e.g. an APACHE score) which summarizes the patient's condition.

The density maps can be used both in a manual form (similar to a nomogram) and with the aid of a computer.

PRACTICAL EXAMPLE 1

(1) The measured values for the indicator substances in the blood plasma of a person are recorded in the first process step. The following list of data is obtained:

TABLE 1

| Indicator substance | Measured value |
|---|---|
| cPSA | 3 µg/L |
| tPSA | 4.2 µg/L |

Figure 2:
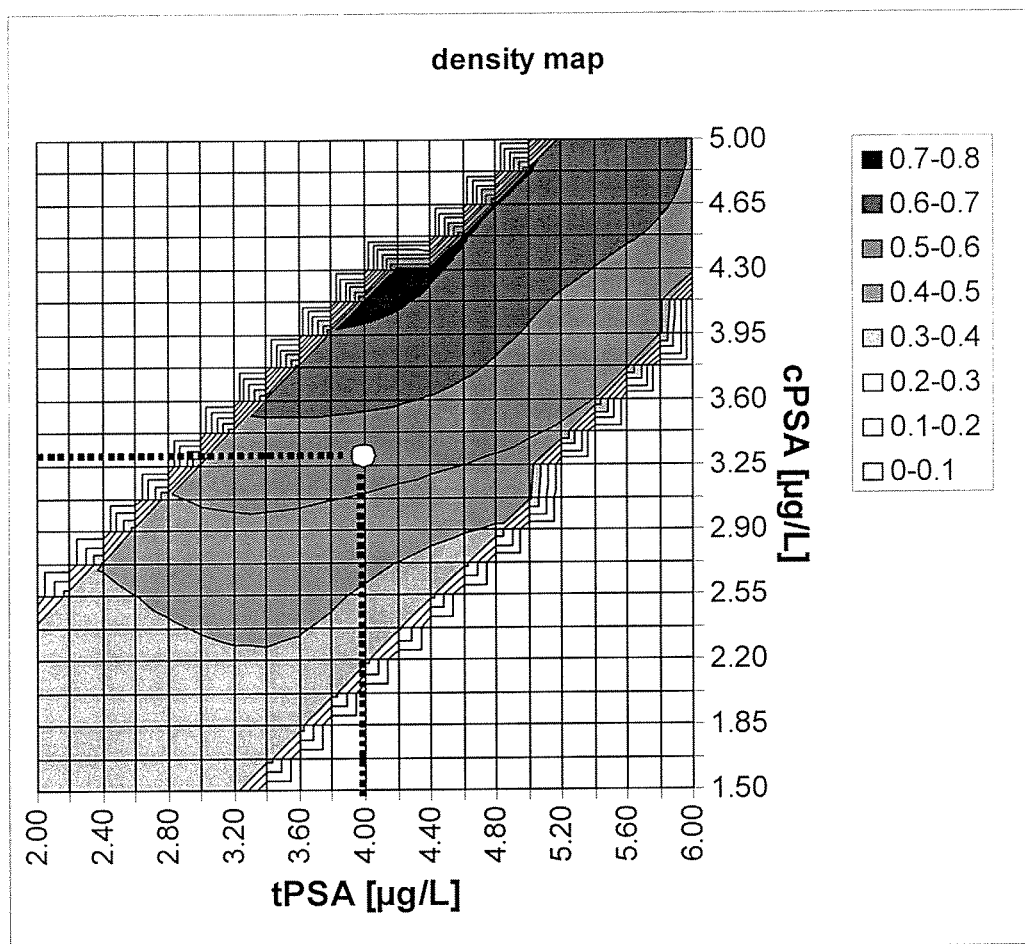

(2) In the second process step the measured values are recorded in a scatterplot. The plotted values are shown in FIG. 1.
(3) In this process step the position in the scatterplot is assigned to a density with the aid of the stored, diagnostically confirmed data blocks which have been mathematically processed with the aid of the kernel-density method and form a density map in the said scatterplot (see FIG. 2). This can be carried out computationally or in the form of a nomogram.

The mathematical processing of the stored, diagnostically confirmed data blocks is carried out by:
a) selecting the data base and applying it to a clinical use situation: tPSA and cPSA data from the use situation: "Initial clinical diagnosis for suspected prostate carcinoma";
b) subdividing the measurement range into a grid (in the present case 20×20 subdivisions);
c) calculating the kernel densities $D_{dis}$ of the prostate carcinoma (PCA) cases and $D_{nondis}$ of the (nPCA) cases not suffering from prostate carcinoma for each grid dot according, for example, to Härdle 2003, for which a Gaussian kernel is used, and calculating the line width according to the "Thumbs Rule" stated in the reference. (Reference: Härdle W, Simar L: Applied Multivariate Statistical Analysis, Springer-Verlag, Berlin Heidelberg 2003, pp. 25 et seq.);
d) determining the quotients $D_{dis}/(D_{dis}+D_{nondis})$ for each grid dot and
e) producing a diagram with a suitable computer program.

The measured values are assigned to a density range of 0.5-0.6 (cf. FIG. 2)
(4) The density range corresponds to a positive prognostic value of 50-60% for the patent's risk of suffering from prostate carcinoma.

PRACTICAL EXAMPLE 2

(1) The measured values for the indicator substances in a person's blood plasma are recorded in the first process step. The following list of data is obtained:

TABLE 2

| Indicator substance | Measured value |
|---|---|
| tPSA | 6.2 µg/l |
| fPSA/tPSA % | 16% |

Figure 3:
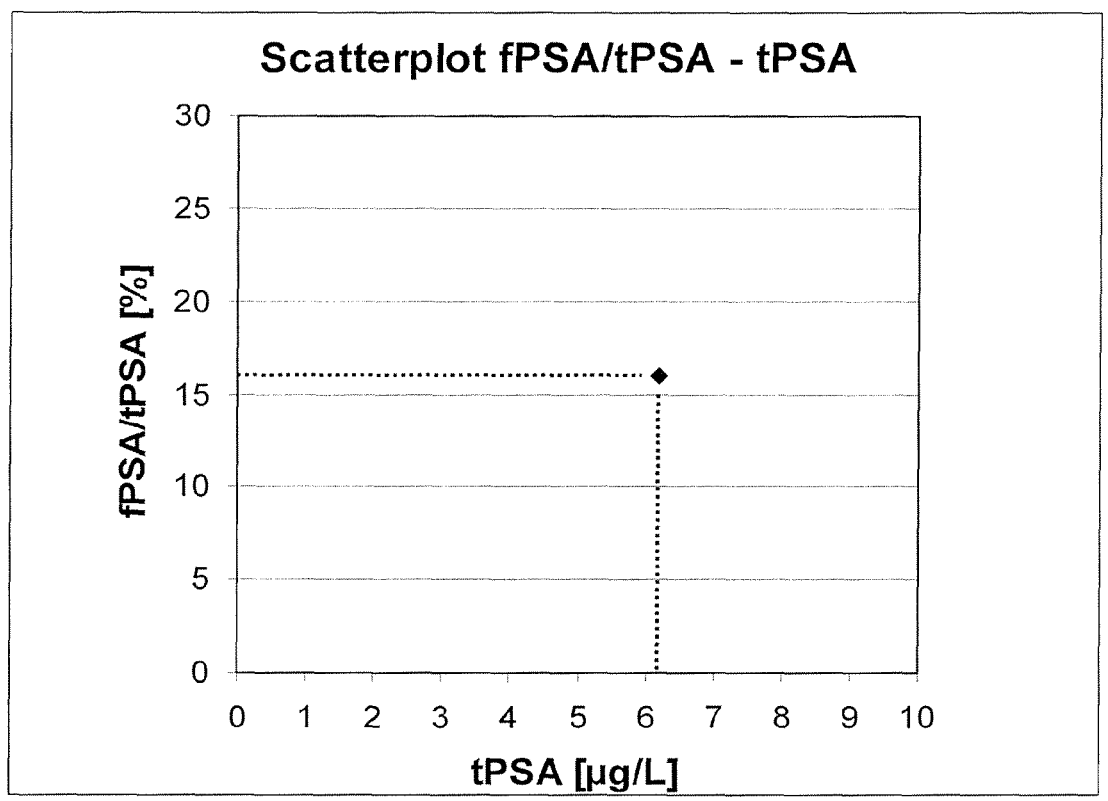
Figure 4:
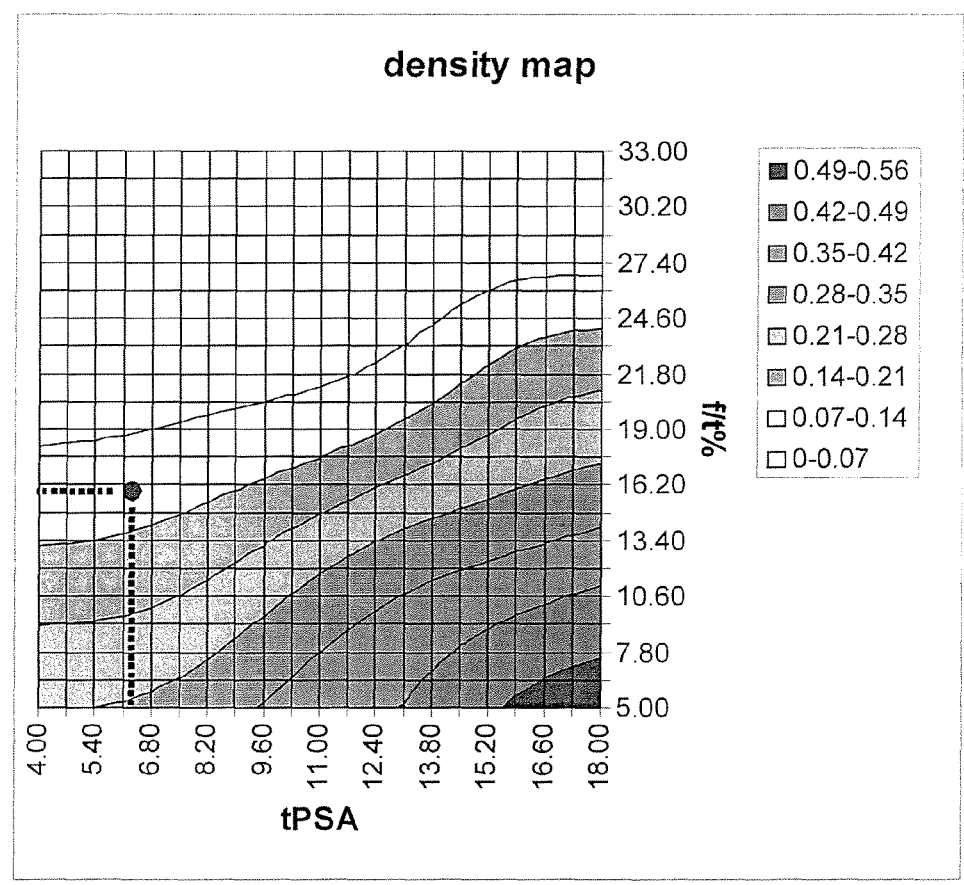

(2) In the second process step the measured values are recorded in a scatterplot. The plotted value are shown in FIG. 3.
(3) In this process step the position in the scatterplot is assigned to a density together with the stored diagnostically confirmed data blocks which have been mathematically processed with the aid of the kernel-density method and form a density map in the said scatterplot (see FIG. 4). This can be carried out computationally or in the form of a monogram.

The mathematical processing of the stored, diagnostically confirmed data blocks is carried out by:
a) selecting the database and applying it to a clinical use situation: tPSA and cPSA data from the use situation: "Initial clinical diagnosis for prostate carcinoma".
b) subdividing the measurement range into a grid (in the present case 20×20 subdivisions);
c) calculating the kernel densities $D_{dis}$ of the PCA cases and $D_{nondis}$ of the nPCA cases for each grid dot according, for example, to Härdle 2003 for which a Gaussian kernel is used and calculating the line width according to the "Thumbs Rule" stated in the reference, (Reference: Härdle W. Simar L: Applied Multivariate Statistical Analysis, Springer-Verlag Berlin Heidelberg 2003, pp. 25 et seq.);
d) determining the quotients $D_{dis}/(D_{dis}+D_{nondis})$ for each grid dot;
e) producing a diagram with a suitable computer program.

The measured values are assigned to a density range of 0.07-0.14.
(4) The density range corresponds to a positive prognostic value of 7-14% for the patient's risk of suffering from prostate carcinoma.

PRACTICAL EXAMPLE 3

(1) The measured values for the indicator substances in a person's blood plasma are recorded according to a first process step. The following list of data is obtained:

TABLE 3

| Indicator substance, indicator value | Measured value |
|---|---|
| cPSA | 3 µg/L |
| tPSA | 4.2 µg/L |
| Prostate volume | 62 cm³ |

Figure 5A:
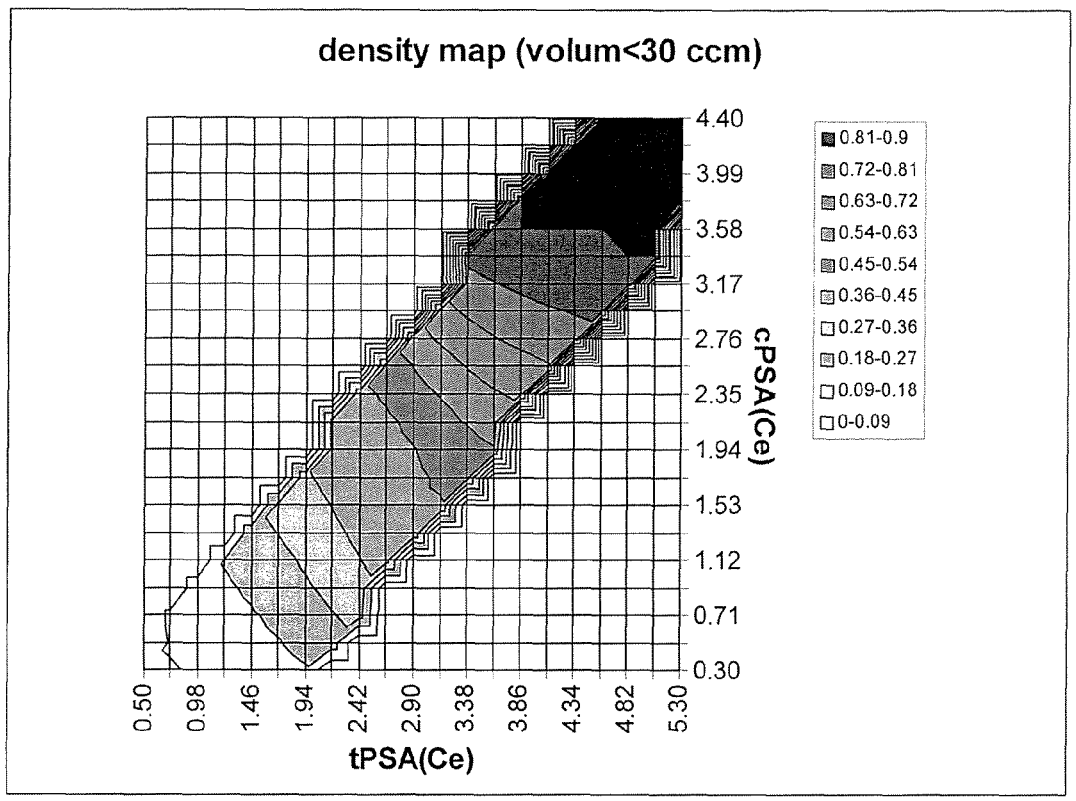
Figure 5B:
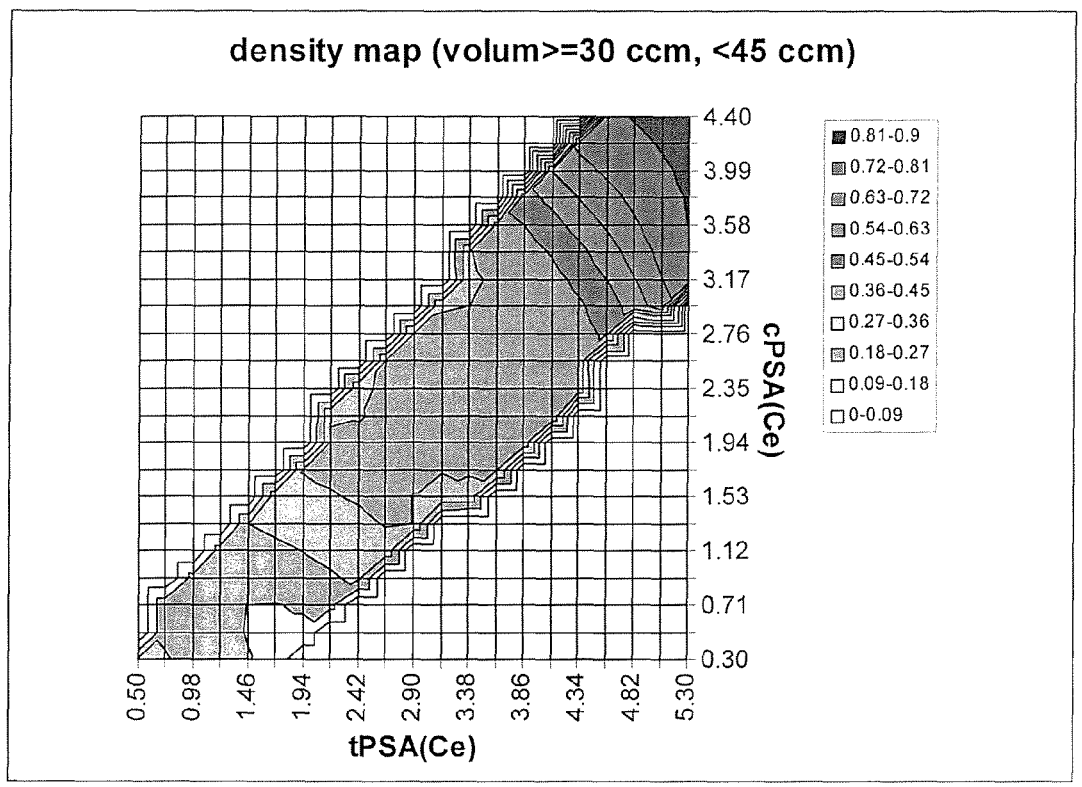
Figure 5C:
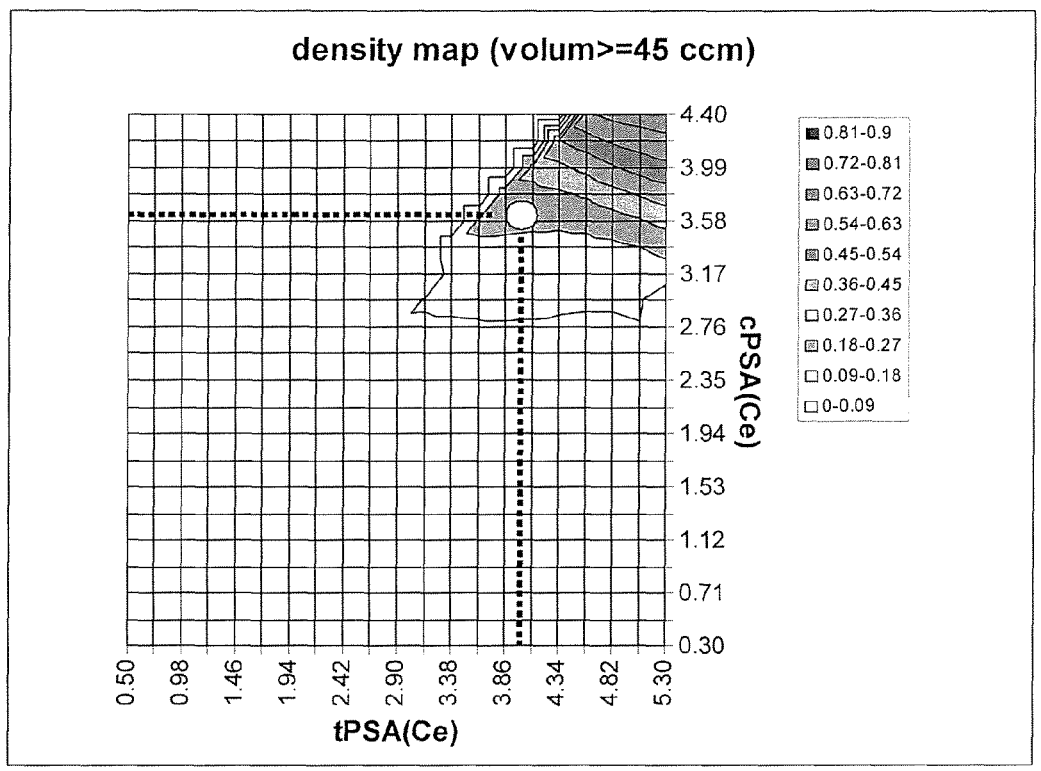

(2) In the second process step the measured values are recorded in a 3 D scatterplot. In the present case the 3 D scatterplot is subdivided into several layers (segments) which are each presented as a 2 D scatterplot (e.g. FIG. 5).
(3) In this process step the position in the scatterplot is assigned to a density with the aid of the stored, diagnostically confirmed data blocks which have been mathematically processed with the aid of the kernel-density method and form a density map in the said scatterplot. This can be carried out computationally or in the form of a nomogram.

The mathematical processing of the stored, diagnostically confirmed data blocks is carried out by:

a) selecting the database and applying it to a clinical use situation:
tPSA and cPSA data form the use situation:
"Initial clinical diagnosis for suspected prostate carcinoma";
b) subdividing the measurement range into a grid (in the present case 20×20 subdivisions);
c) calculating the kernel densities $D_{dis}$ of the PCA cases and $D_{nondis}$ of the nPCA cases for each grid dot according, for example, to Härdle 2003 for which a Gaussian kernel is used, and calculating the line width according to the "Thumbs Rule" stated in the reference, (Reference: Härdle W, Simar L: Applied Multivariate Statistical Analysis, Springer-Verlag Berlin Heidelberg 2003, pp. 25 et seq.);
d) determining the quotients $D_{dis}/\!/D_{dis}+D_{nondis}$ for each grid dot;
e) producing the 3D diagram or the 2D diagram layers with a suitable computer program.

The measured values are assigned to a density range of 0.18-0.27 on the density layer >45 ccm corresponding to the prostate volume.

(4) The density range corresponds to a positive prognostic value of 18-27% for the patient's risk of suffering from prostate carcinoma, (i.e. far lower than in practical example 1, despite the same tumour marker values).

A method of assessing a patient's risk of suffering from a disease using n indicator substances from body fluids may be characterized in that:

a) n is >1,
b) the measured values for n indicator substances are plotted in an n-dimensional system of coordinates to give the dot ($x_1, x_2, \ldots, x_n$),
c) in this system of coordinates, curves or areas are calculated which represent polynomials of the $m^{th}$ degree for the indicator substance k (k consisting arbitrarily of 1, . . . , n) as a function of the remaining n−1 indicator substances (1, . . . , k−1, k+1, . . . , n) and are distinguished by the fact that they are curves or areas of identical functional values y for one function y=f($x_1, x_2, \ldots, x_n$), the function y being obtained from the quotient of the density areas calculated by the kernel density method for (i) diseased patients and (ii) the sum total of diseased and non-diseased patients in a study population plotted in the n-dimensional system of coordinates,
d) from the sum total of the calculated curves or areas a subgroup of p curves or areas is selected,
e) a value between the functional values represented by the two next adjacent curves or areas of the subgroup is assigned to the dot ($x_1, x_2, \ldots, x_n$) and this assigned value corresponds to a specific risk of having a disease.

The invention claimed is:

1. A method of assessing a patient's risk of suffering from a disease using indicator substances −n from body fluids comprising the steps of:
a) recording, with a computer, measured values for the indicator substances n in an n-dimensional system of coordinates represented by ($X_1, X_2 \ldots X_n$),
b) calculating, by the computer, in the n-dimensional system of coordinates, curves or areas representing polynomials of an mth order for an indicator substance k (k consisting arbitrarily of 1, . . . , n) as a function of the remaining n−1 indicator substances (1, . . . , k−1, k+1, . . . , n), the curves or areas being of identical functional values y for a function y=f ($X_1, X_2, \ldots, X_n$), the function y being a measure of risk calculated using a kernel density method of ($X_1, X_2, \ldots, X_n$)=$D_d(X_1, X_2, \ldots, X_n)/(D_d(X_1, X_2, \ldots, X_n)+D_n(X_1, X_2, \ldots, X_n))$ where $D_d(X_1, X_2, \ldots, X_n)$ is a first density for the probability distribution of diseased patients from a study population and $D_n(X_1, X_2, \ldots, X_n)$ is a second density for the probability distribution of non-diseased patients from the study population, and
c) assigning a value corresponding to a specific risk y1 of having a disease based on a location of the measured values within the n-dimensional system of coordinates, the specific risk y1 being between functional values represented by two next adjacent curves or areas of a subgroup of the curves or areas.

2. The method according to claim 1, characterized in that the assigned value in step c) is a mean value between the functions y for the measured values.

3. The method according to claim 1, characterized in that the study population in claim 1, step b) is used for setting cut-off values for individual indicator values for diagnosing the disease.

4. The method according to claim 1, characterized in that the disease is prostate carcinoma and the indicator substances are selected from the group consisting of cPSA, tPSA, fPSA, BPSA, proPSA, intact-PSA, PSA-API, PSA-ACT, PSA-alpha-2M, and combinations and ratios thereof.

5. The method according to claim 1, characterized in that additional smoothing processes, weighting processes and processes for controlling outliers are used for the calculation according to the kernel density method of claim 1, step b).

6. The method according to claim 1, characterized in D that at least one additional parameter specifically associated a tumourous disease is included in the analysis.

7. The method according to claim 4, wherein the indicator substances are cPSA and tPSA.

8. The method according to claim 4, wherein the indicator substances are tPSA and a ratio of fPSA/tPSA.

9. The method according to claim 6, characterized in that the disease is prostate carcinoma and the at least one additional parameter is prostate volume.

* * * * *